United States Patent [19]
Tomita

[11] Patent Number: 5,468,514
[45] Date of Patent: Nov. 21, 1995

[54] METHOD OF PRODUCING A PH-RESPONSIVE MEMBRANE

[75] Inventor: Katsuhiko Tomita, Ohtsu, Japan

[73] Assignee: Horiba, Ltd., Kyoto, Japan

[21] Appl. No.: 273,635

[22] Filed: Jul. 12, 1994

Related U.S. Application Data

[63] Continuation-in-part of Ser. No. 797,907, Nov. 26, 1991, abandoned.

[30] Foreign Application Priority Data

Nov. 30, 1990 [JP] Japan .................................. 2-339487

[51] Int. Cl.$^6$ ........................................................ B05D 5/12
[52] U.S. Cl. ..................... 427/77; 427/126.3; 427/226; 427/240; 427/243; 427/430.1
[58] Field of Search ............................. 427/240, 226, 427/243, 430.1, 77, 126.3

[56] References Cited

U.S. PATENT DOCUMENTS

| | | | |
|---|---|---|---|
| 4,019,011 | 4/1977 | Cape | 219/76 |
| 4,378,953 | 4/1983 | Winn | 359/894 |
| 4,835,023 | 5/1989 | Taniguchi et al. | 427/157 |
| 4,909,912 | 3/1990 | Oda et al. | 427/201 |
| 4,937,055 | 6/1990 | Kittler et al. | 427/126.3 |
| 5,112,676 | 5/1992 | Cot et al. | 427/126.2 |

FOREIGN PATENT DOCUMENTS

WO8809501  5/1988  WIPO.

OTHER PUBLICATIONS

Patent Abstract of Japan, vol. 7, No. 57(p. 181)(1202), 9 Mar. 1983 & JP-A-57 203 946 (Olympus Kogaku Kogyo) 14 Dec. 1982 *abstract*.

Materials Research Society Symposia Proceedings, vol. 73, 1986, Pittsburgh US pp. 725–730; L. A. Silverman et al. 'Characterization of sol-gel derived tantalum oxide films' *the whole document* & Better Ceramics Through Chemistry II Symposium 15–19 Apr. 1986, Palo Alto US.

Materials Research Society Symposia Proceedings vol. 180, 1990, Pittsburgh US pp. 611–616; H. Hirashima et al.; 'Densification and crystallization of thin transition metal oxide coatings from metal alkoxides' *the whole document* & Better Ceramics Through Chemistry IV Symposium 15–20 Apr. 1990. San Francisco US.

*Primary Examiner*—Janyce Bell
*Attorney, Agent, or Firm*—Price Gess & Ubell

[57] ABSTRACT

A method of producing a pH-responsive membrane by coating a substrate with an anhydrous coating solution of tantalum alkoxide. In a first preferred embodiment, an anhydrous tantalum alkoxide solution is deposited drop by drop on a surface of an electrode substrate which is rapidly rotating to form a film of tantalum alkoxide. After drying to remove the solvent, the electrode is baked to decompose the tantalum alkoxide, thereby forming a pH-responsive membrane of tantalum pentoxide. The thickness of this membrane can be controlled by altering the speed of substrate rotation and the volume of coating solution deposited thereon. In a second preferred embodiment, an electrode substrate is immersed in an anhydrous coating solution of a tantalum alkoxide followed by pulling the electrode substrate from the solution at a controlled rate to form a tantalum alkoxide film which is then converted to a pH-responsive membrane of tantalum pentoxide by drying and baking.

18 Claims, 4 Drawing Sheets

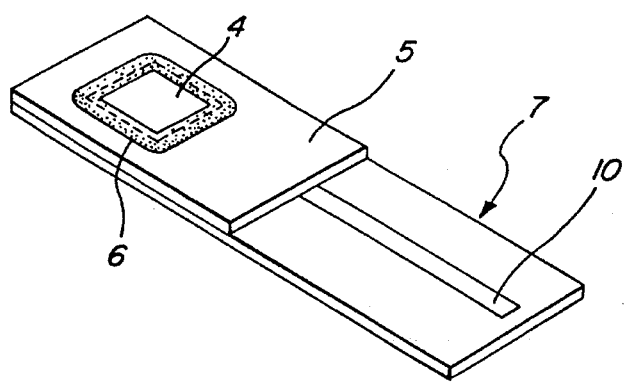
FIG. 3A
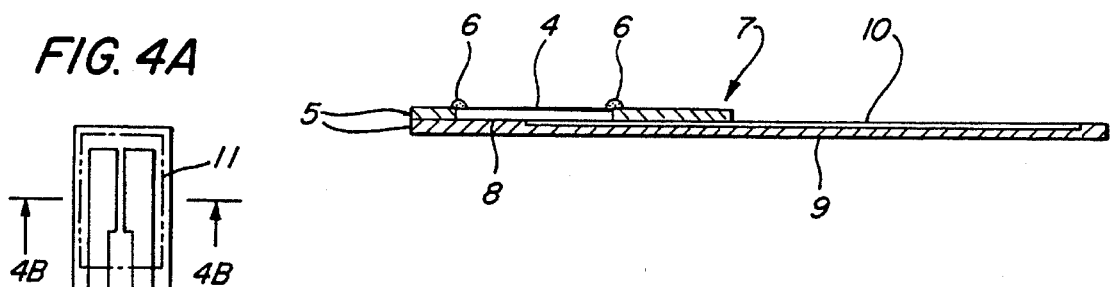
FIG. 3B
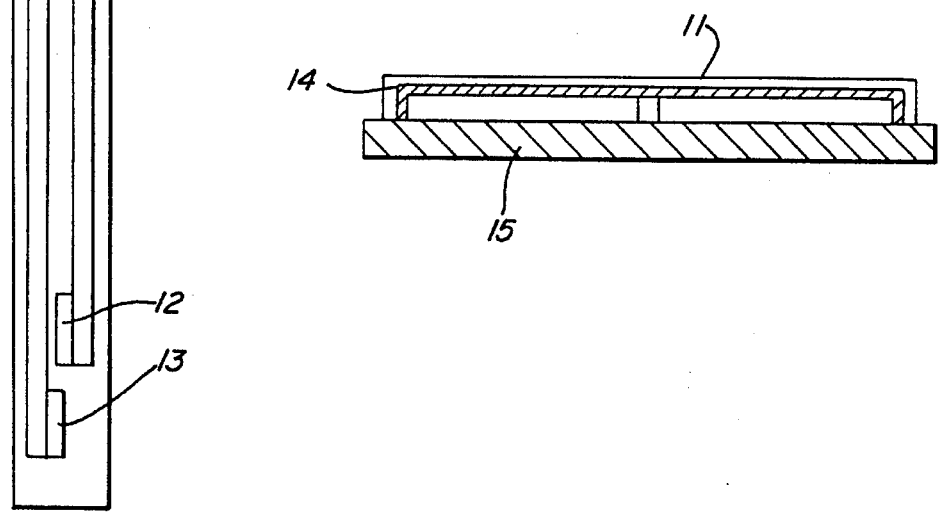
FIG. 4A
FIG. 4B

METHOD OF PRODUCING A PH-RESPONSIVE MEMBRANE

This application is a continuation-in-part of application Ser. No. 07/797,907 filed Nov. 26, 1991, now abandoned.

BACKGROUND OF THE INVENTION

1. Field of the Invention

The present invention relates to a method for producing a pH-responsive membrane and, in particular, to a method for producing a pH-responsive membrane formed of a thin membrane of tantalum pentoxide.

2. Description of Related Art

A conventional method for producing a pH-responsive membrane is disclosed in Japanese Patent Application No. Sho 63-312736, filed Dec. 10, 1988 for METHOD OF PRODUCING ION SELECTIVE GLASS ELECTRODE. Japanese Application No. Sho 63-312736, filed by the instant Applicant, discloses a method in which a metal alkoxide is used as a raw material in a sol-gel method for producing a pH-responsive membrane. This conventional method is advantageous in its production of a stabilized pH-responsive membrane, but the method entails an expensive and complicated manufacturing process. Furthermore, the method employs a coating solution that is not stable.

OBJECTS AND SUMMARY OF THE INVENTION

It is, therefore, an object of the present invention to provide an easy and inexpensive method for producing a pH-responsive membrane;

It is a further object of the invention to provide a method for producing a pH-responsive membrane having a uniform thickness; and It is yet a further object of the present invention to provide a method for producing a pH-responsive membrane which allows one the option of altering the membrane thickness without requiring the use of a large scale apparatus.

These and other objects of the invention are met by a method for producing a pH-responsive membrane wherein a substrate is coated with an anhydrous coating solution of tantalum alkoxides in a solvent in a manner that allows the amount of coating solution applied to be accurately controlled. Following the coating step, the coated substrate is dried and heated, which converts a tantalum alkoxide film to a pH-responsive membrane of tantalum pentoxide.

In a first preferred embodiment, the electrode substrate is rapidly rotated by a motor and the anhydrous coating solution is deposited on the spinning substrate drop by drop to form a thin film of tantalum alkoxide. In this method the film thickness can be readily varied by altering the speed of rotation of the electrode substrate and the number of drops of the coating solution deposited on the substrate.

A second preferred method of the present invention forms a tantalum alkoxide film by immersing the electrode substrate in an anhydrous coating solution comprised of tantalum alkoxide in an anhydrous solvent. The electrode substrate is then pulled from the coating solution at a controlled speed to form the tantalum alkoxide film. The speed with which the electrode substrate is removed from the coating solution determines the thickness of the responsive membrane left upon the electrode substrate after drying and heating.

In the first and second methods according to the preferred embodiments of the present invention, the pH-responsive membrane is created upon the electrode at a desired thickness, either by altering the speed of rotation in the spin coating method, or by altering the speed of the pulling in the immersion pull method. Once the film is formed upon the electrode substrate, the film is subjected to the steps of drying and then baking and curing to create the desired tantalum pentoxide membrane.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 3(A) is a diagram showing a perspective view of one example of a pH-measuring electrode having a pH-responsive membrane produced by the first preferred embodiment of the present invention;

FIG. 3(B) is a cross-sectional view of the pH-measuring electrode illustrated in FIG. 3(A);

FIG. 4(A) is a plan view of one example of a pH-measuring electrode having a pH-responsive membrane produced by the first preferred method of the present invention;

FIG. 4(B) is a cross-sectional view of the pH-measuring electrode illustrated in FIG. 4(A), taken along the line A—A;

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein to produce a pH-responsive membrane of tantalum pentoxide by coating a substrate with an anhydrous solution of a tantalum alkoxide in an appropriate solvent.

Figure 1:
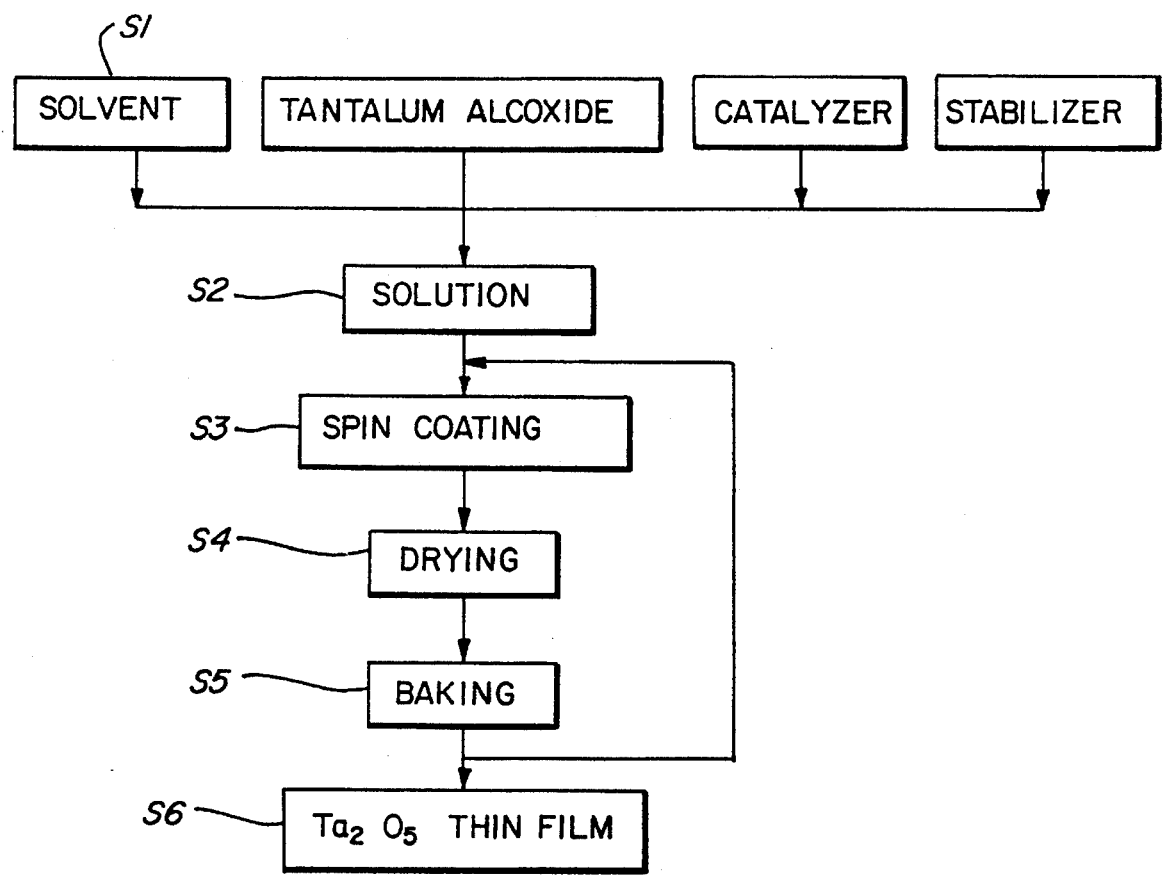
FIG. 1 is a flow chart showing a method of spin coating to produce a pH-responsive membrane according to the first preferred embodiment of the present invention.
Figure 2:
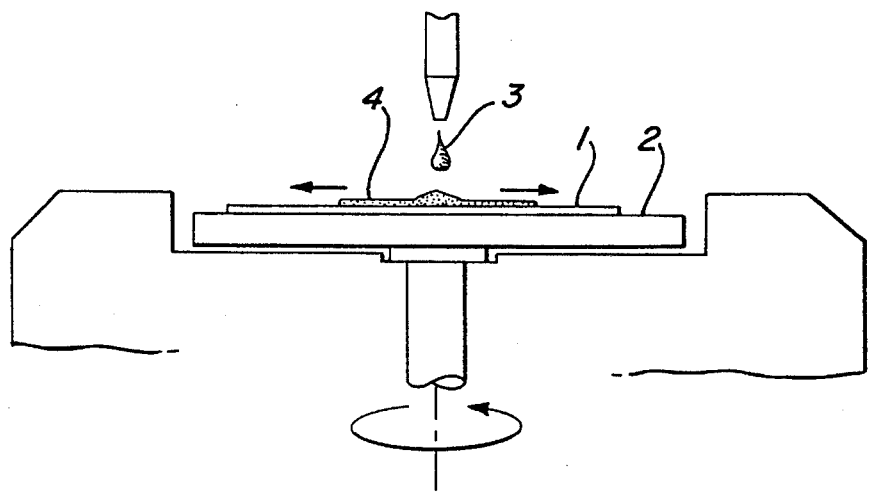
FIG. 2 is a cross-sectional diagram showing the spin coating method of creating a thin film on an electrode substrate.

A first preferred embodiment of the present invention is illustrated in FIGS. 1–3. As shown in FIG. 1, a coating solution is created wherein pentaethoxy tantalum [Ta-$(OC_2H_5)_5$] is used as a tantalum alkoxide [Ta-$(O-R)_5$] and is dissolved in anhydrous ethyl alcohol as a solvent in a quantity of 10% by weight (5% by weight of $Ta_2O_5$). A catalyst consisting of anhydrous acetic acid and a stabilizer consisting of acetyl acetone are added to the tantalum alkoxide solution in a quantity by weight corresponding to two times the molar ratio of the pentaethoxy tantalum. The combination and mixing of these compounds are shown in Step S1 of FIG. 1. In this step the coating solution (S2) is created by dissolving an organotantalum compound is an anhydrous solvent. After mixing, the coating solution is maintained as moisture-free (i.e., stored under anhydrous conditions).

In Step S3 of FIG. 1, as shown in FIG. 2, the resulting coating solution is deposited, drop by drop, on a spinning electrode substrate 1. In FIG. 2 a metallic layer, such as gold, has been deposited on a bottom surface of a silicon wafer, and a naturally-formed oxidized layer upon the upper surface has been removed to create the electrode substrate 1.

The electrode substrate 1 is placed upon a disk 2 and spun by a motor (not shown). The electrode substrate 1 is held horizontally with the surface to be coated facing upward. The disk 2 is rotated, for example, for 30 seconds at 3,000 rpm, while about 100 μl to 200 μl of the coating solution 3 are dropped from above and spread by centrifugal force to create a thin film.

Thereafter, the electrode substrate 1, which has been spin coated as discussed above, is dried for approximately 30 minutes at 150° C. (Step S4 shown in FIG. 1), and then heat treated or baked (Step S5 shown in FIG. 1) for 30 minutes at 500° C. to form a tantalum pentoxide ($Ta_2O_5$) membrane 4 on the surface of the electrode substrate 1.

Tantalum alkoxide (specifically pentaethoxy tantalum in this embodiment) is the main ingredient of the coating solution 3. Because only a single type of alkoxide is used, it is easy to control the hydrolytic conditions, thereby making the baking conditions uniform and allowing reproducible creation of a thin film having uniform film thickness.

In this embodiment, Steps S3–S5 can be repeated a suitable number of times to increase the thickness of membrane 4. In the preferred embodiment, the membrane 4 is between 600 and 650 Å thick. The thickness of the film 4 can be made highly reproducible by selecting a solvent for the coating solution 3 with consideration of the solvent's ability to wet glass and the silicon substrate, and by controlling the viscosity of the solution and temperature and humidity during the coating process. The presence of water or water vapor during the coating process can lead to pinholes and other film defects and, hence, should be strenuously avoided.

The membrane 4 produced in accordance with the above-described method of the first preferred embodiment will exhibit a resistance value of $10^8$–$10^9$ Ω in pinhole-free cases. Further, the membrane 4 produced in this manner will have the pH-responsive characteristics illustrated in FIG. 7.

A pH-measuring electrode 7, for measuring a liquid's pH after immersing the electrode 7 in the liquid, is illustrated in FIGS. 3(A) and 3(B). This pH-measuring electrode 7 is created by using a silicone resin adhesive 6 to seal the membrane 4 to a base 5 of laminated polyethylene terephthalate. As shown in FIGS. 3(A) and 3(B), the pH-measuring electrode 7 also comprises a silicon substrate 8 for an ISFET (Ion Selective Field Effect Transistor), a further silicon substrate 9, and a lead attachment conductor 10.

As described above, the first preferred embodiment uses pentaethoxy tantalum as the tantalum alkoxide. However, other tantalum alkoxides may be used, such as penta-x-butoxytantalum [$Ta(OC_4H_9)_5$] (wherein x may be equal to i [iso], n [normal], sec [secondary] or t [tertiary]), any of which may be used in place of the pentaethoxy tantalum.

To make the solution, penta-x-butoxy tantalum is dissolved in anhydrous ethyl alcohol as a solvent in a quantity of 20% by weight (10% by weight of $Ta_2O_5$). A catalyst such as formic acid or hydrochloric acid, and a stabilizer, such as diethyl malonate or ethyl acetoacetate are added to the resulting solution in a quantity equivalent to four times the molar ratio of the tantalum for the catalyst and one times the molar ratio for the stabilizer. The ingredients are then mixed in a moisture-free environment (i.e., under anhydrous conditions) to create the coating solution.

This coating solution is applied to the substrate using the same spin coating steps as discussed above and illustrated in FIG. 1. The membrane created in this manner will also exhibit pH-responsive characteristics similar to those shown in FIG. 7.

The thin film created using this pentabutoxy tantalum solution may be used to create a responsive membrane for either a gate-oxidized ISFET or a separated gate-type ISFET. In the packaging structure shown in FIG. 4, a thin tantalum membrane 11 is created above a source electrode 12 and a drain electrode 13, each comprised of aluminum. An insulating silicon dioxide [$SiO_2$] layer 14 is created on an upper surface of a silicon substrate 15 to keep the electrodes 12, 13 electrically isolated.

In this structure, the pentabutoxy tantalum may be replaced with penta-i-propoxytantalum or penta-n-propoxytantalum. It should also be understood that the tantalum membranes 4, 11 shown in FIGS. 3 and 4, respectively, may also be formed by the immersion pull method, discussed below, as well as the spin coating method.

Figure 5:
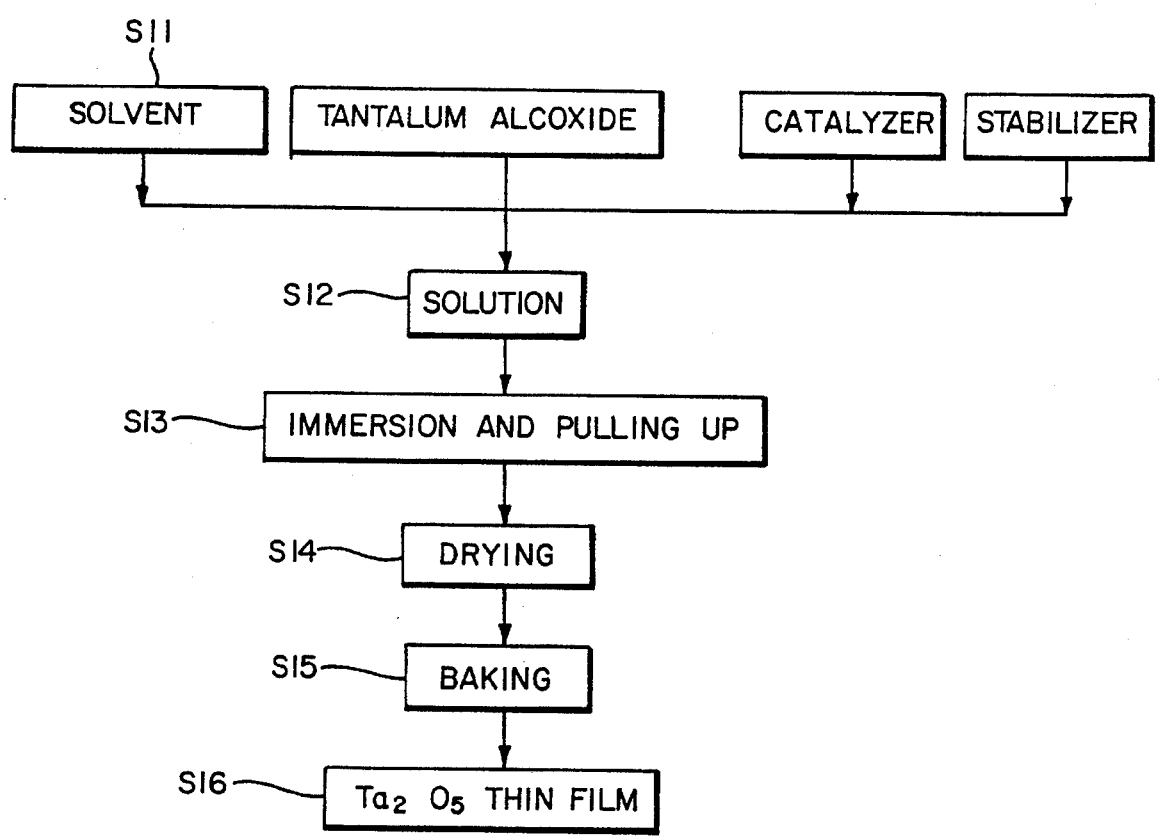
FIG. 5 is a flow chart showing a method of producing a pH-responsive membrane according to the immersion pull method of the second preferred embodiment of the present invention.
Figure 6:
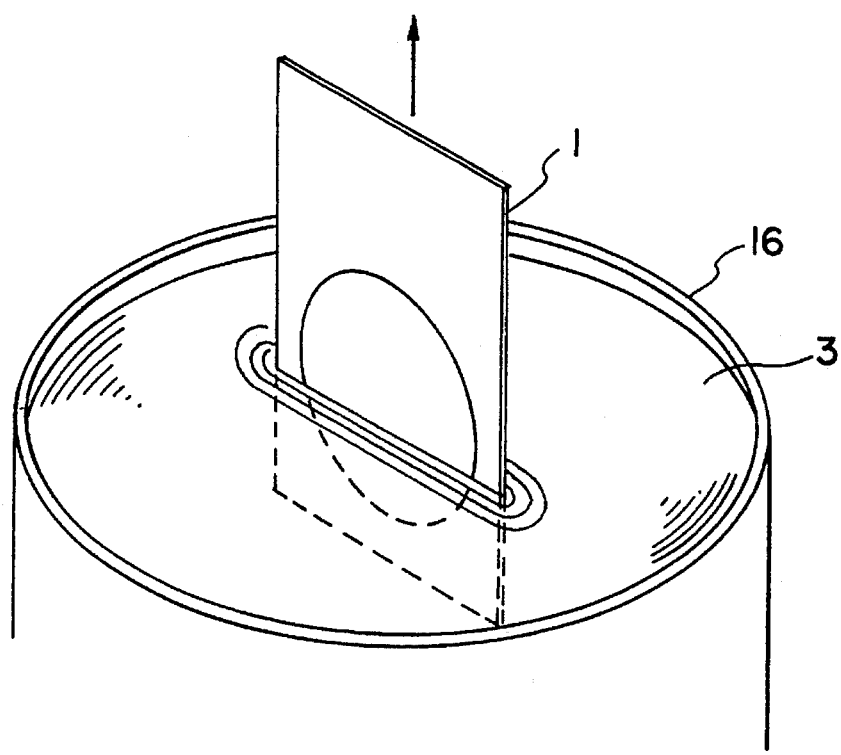
FIG. 6 is a diagram illustrating the forming of the thin film by the immersion pull method of an electrode substrate as disclosed in the second preferred embodiment of the present invention.

The immersion pull method for creating a pH-responsive thin film in accordance with a second preferred embodiment of the invention is illustrated in FIGS. 5 and 6. In this embodiment, pentamethoxy tantalum [$Ta-(OCH_3)_5$] is used as the tantalum alkoxide. It is dissolved in anhydrous ethyl alcohol as a solvent in a quantity of 5% by weight. Acetic acid, as a catalyst, and ethyl acetoacetate, as a stabilizer, are then added to the resulting solution in a quantity corresponding to two times the molar ratio of the pentamethoxy tantalum. The solution is then mixed in a moisture-free environment (i.e., an anhydrous environment) to create the coating solution 3 as shown in Steps S11 and S12 illustrated in FIG. 5.

In the immersion pull method illustrated in FIGS. 5 and 6, 20 ml of the coating solution 3 are placed in a beaker 16, as shown in FIG. 6. An electrode substrate 1 is immersed in the coating solution 3 and then pulled from the solution 3 at a rate of 0.1–0.6 mm/sec to form a thin film of tantalum alkoxide on the electrode substrate 1 (Step S13). Pulling at the slower speed yields a thicker tantalum film.

Figure 7:
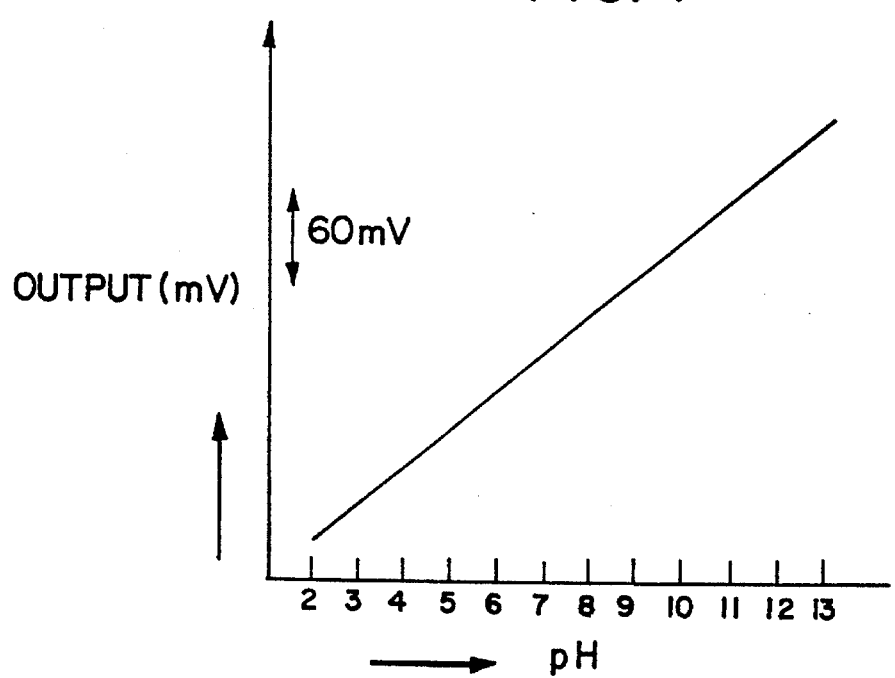
FIG. 7 is a diagram showing the pH-responsive characteristics of a thin film produced in accordance with the present invention.

The electrode substrate 1 is then dried, to remove the solvent, for 30 minutes at 150° C. (Step S14), and heat treated for 30 minutes at 500° C. (Step S14) to form a tantalum pentoxide [$Ta_2O_5$] membrane having the required film thickness on the surface of electrode substrate 1. The membrane produced in the immersion pull method discussed above will exhibit a pH-responsive characteristic, as shown in FIG. 7.

The pH-responsive membrane created using either the spin coating method or the immersion pull method exhibits the following advantages: (1) uniform membranes are quickly and easily formed; (2) only a small amount of the expensive coating solution is wasted; and (3) membrane thickness can be optionally varied and easily produced in an inexpensive manner without requiring a large and expensive apparatus.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A method for producing a pH-responsive membrane, comprising the steps of:

preparing an anhydrous coating solution of tantalum alkoxide, an anhydrous solvent, a stabilizer, and a catalyst;

providing an electrode substrate;

coating the electrode substrate with the anhydrous coating solution under anhydrous conditions to form a film of tantalum alkoxide;

drying the coated substrate to remove the solvent; and heating the dried coated substrate to decompose the tantalum alkoxide, thereby forming a pH-responsive membrane of tantalum pentoxide.

2. The method of claim 1, wherein the tantalum alkoxide is selected from the group consisting of pentaethoxy tantalum, pentamethoxy tantalum, penta-n-propoxy tantalum, penta-iso-propoxy tantalum, penta-n-butoxy tantalum, penta-sec-butoxy tantalum, penta-iso-butoxy tantalum and penta-tert-butoxy tantalum.

3. The method of claim 1, wherein the catalyst is selected from the group consisting of formic acid, acetic acid, and hydrochloric acid.

4. The method of claim 1, wherein the stabilizer is selected from the group comprising acetyl acetone, diethyl malonate and ethyl acetoacetate.

5. The method of claim 1, wherein the step of coating the substrate includes depositing the coating solution onto a rotating substrate drop by drop.

6. The method of claim 5, further including the step of controlling the film thickness by altering a volume of the solution that is dropped and a duration over which the solution is dropped.

7. The method of claim 6, wherein the substrate is held in a horizontal plane and rotated for 30 seconds at 3,000 rpm.

8. The method of claim 1, wherein the membrane thickness is increased by repeating the steps of coating, drying, and heating.

9. The method of claim 1, wherein the step of coating the substrate includes immersing the substrate in the coating solution and pulling the substrate from the solution.

10. The method of claim 9, further including the step of controlling the film thickness by altering a speed with which the substrate is pulled from the coating solution from about 0.1 mm/sec to about 0.6 mm/sec.

11. The method of claim 10, wherein the substrate is removed from the coating solution at a rate of 0.1–0.6 mm/sec.

12. A method of producing a pH-responsive membrane comprising the steps of:

providing an electrode substrate;

preparing an anhydrous liquid coating solution of tantalum alkoxide, anhydrous ethyl alcohol, acetyl acetone, and acetic acid;

coating the electrode with the anhydrous coating solution;

drying the coated electrode substrate at approximately 150° C. for about 30 minutes; and baking the dried coated electrode substrate at approximately 500° C. for about 30 minutes, thereby producing a pH-responsive membrane of tantalum pentoxide on the electrode.

13. The method of claim 12, wherein the step of coating the substrate includes depositing the coating solution onto the substrate while it is rotated at 3,000 rpm.

14. The method of claim 12, wherein the step of coating the substrate includes immersing the substrate in the coating solution and pulling the substrate from the coating solution at a rate of about 01.-0.6 mm/sec.

15. The method of claim 12, wherein the membrane thickness is increased by repeating the steps of coating, drying, and heating.

16. The method of claim 12, wherein the tantalum alkoxide is selected from the group consisting of pentaethoxy tantalum, pentamethoxy tantalum, penta-n-propoxy tantalum, penta-iso-propoxy tantalum, penta-n-butoxy tantalum, penta-sec-butoxy tantalum, penta-iso-butoxy tantalum and, penta-tert-butoxy tantalum.

17. A method for producing a pH-responsive membrane, comprising the steps of:

preparing an anhydrous coating solution comprising about 10% by weight pentaethoxy tantalum alkoxide, about 3% by weight anhydrous acetic acid, and about 5% by weight anhydrous acetylacetone in anhydrous ethyl alcohol;

providing an electrode substrate;

attaching the substrate to a device which spins the substrate at about 3,000 rpm;

coating the electrode substrate with the anhydrous coating solution under anhydrous conditions by depositing the solution drop by drop on the spinning to form a film of pentaethoxy tantalum;

drying the coated substrate to remove the solvent; and heating the dried coated substrate to about 500° C. to decompose the pentaethoxy tantalum, thereby forming a pH-responsive membrane of tantalum pentoxide.

18. A method for producing a pH-responsive membrane, comprising the steps of:

preparing an anhydrous coating solution comprising about 5% by weight pentamethoxy tantalum alkoxide, about 2% by weight anhydrous acetic acid, and about 4% by weight anhydrous ethyl acetoacetate in anhydrous ethyl alcohol;

providing an electrode substrate;

coating the electrode substrate with the anhydrous coating solution under anhydrous conditions to form a film of methoxy tantalum by immersing the substrate in the coating solution and pulling it from the solution at 0.1–0.6 mm/sec;

drying the coated substrate to remove the solvent; and heating the dried coated substrate to about 500° C. to decompose the methoxy tantalum, thereby forming a pH-responsive membrane of tantalum pentoxide.

* * * * *